United States Patent
Sioss et al.

(10) Patent No.: US 8,728,502 B2
(45) Date of Patent: May 20, 2014

(54) BLACK EFFECT PIGMENT

(75) Inventors: James Sioss, Yorktown Heights, NY (US); Thomas Chirayil, Danbury, CT (US); Betty Aucar, Ossining, NY (US)

(73) Assignee: BASF Corporation, Florham Park, NJ (US)

( * ) Notice: Subject to any disclaimer, the term of this patent is extended or adjusted under 35 U.S.C. 154(b) by 0 days.

(21) Appl. No.: 13/419,772

(22) Filed: Mar. 14, 2012

(65) Prior Publication Data

US 2012/0237577 A1  Sep. 20, 2012

Related U.S. Application Data

(60) Provisional application No. 61/452,804, filed on Mar. 15, 2011.

(51) Int. Cl.
| | | |
|---|---|---|
| *A61K 8/02* | (2006.01) | |
| *A61K 8/19* | (2006.01) | |
| *A61Q 1/00* | (2006.01) | |
| *A61Q 1/02* | (2006.01) | |
| *A61Q 1/06* | (2006.01) | |
| *A61Q 1/12* | (2006.01) | |
| *A61Q 5/00* | (2006.01) | |
| *A61Q 17/00* | (2006.01) | |
| *A61Q 19/00* | (2006.01) | |

(52) U.S. Cl.
USPC ............ 424/401; 106/31.9; 106/418; 424/59; 424/61; 424/64; 424/69; 424/70.6; 424/70.7; 427/214; 427/269; 427/419.3

(58) Field of Classification Search
None
See application file for complete search history.

(56) References Cited

U.S. PATENT DOCUMENTS

| | | | |
|---|---|---|---|
| 3,926,659 A | 12/1975 | Bernhard et al. | |
| 4,867,793 A * | 9/1989 | Franz et al. | 106/415 |
| 6,017,599 A | 1/2000 | Sakamoto et al. | |
| 6,238,472 B1 | 5/2001 | Andes et al. | |
| 6,290,766 B1 * | 9/2001 | DeLuca et al. | 106/417 |
| 6,616,745 B1 * | 9/2003 | Narvarti et al. | 106/417 |
| 7,060,126 B2 | 6/2006 | Andes et al. | |
| 7,303,622 B2 | 12/2007 | Loch et al. | |
| 2007/0032573 A1 | 2/2007 | Yanagase et al. | |
| 2008/0279796 A1 | 11/2008 | Handrosch et al. | |
| 2010/0203093 A1 | 8/2010 | Bujard et al. | |
| 2011/0269845 A1 | 11/2011 | Bujard et al. | |

FOREIGN PATENT DOCUMENTS

| | | |
|---|---|---|
| EP | 0712718 | 5/1996 |
| FR | 2922893 | 5/2009 |
| GB | 1368756 | 10/1974 |
| JP | 2002146236 | 5/2002 |
| WO | 2009007248 | 1/2009 |
| WO | 2010066605 | 6/2010 |

OTHER PUBLICATIONS

International Search Report dated Oct. 29, 2012.

* cited by examiner

*Primary Examiner* — Frederick Krass
*Assistant Examiner* — Isaac Shomer
(74) *Attorney, Agent, or Firm* — Sheila A. Loggins

(57) ABSTRACT

This disclosure is directed to a black effect pigment and a method of forming said pigment. The pigment comprises a platy substrate coated with $SnO_2$ and/or $SnO_2$ hydrates and $Fe_3O_4$ with an optional coating of metal oxides such as $SiO_2$, $TiO_2$, $ZrO_2$ and $ZnO_2$. The deposition of the $SnO_2$ and/or $SnO_2$ hydrates onto the substrate improves the adhesion and prepares the substrate surface for deposition of the iron oxides onto the platy surface, especially mica surfaces. While the pigment may be used in such applications as coating, powder coating, printing ink, plastic, ceramic material, glass, cosmetic formulation, laser marking pigment, pigment composition or dry preparation, the pigment is especially suitable for cosmetic applications.

20 Claims, 2 Drawing Sheets

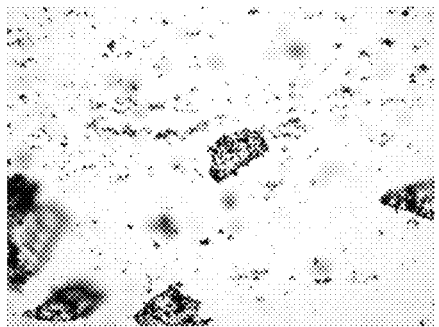
Figure 1 - 0.39 wt.% $SnO_2$, 39 wt.% $Fe_3O_4$
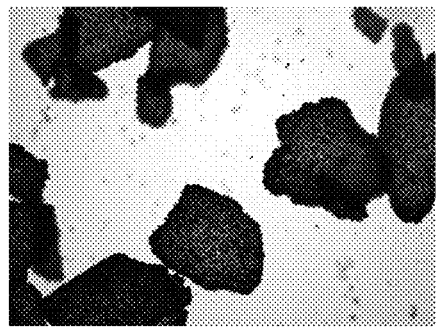
Figure (4) – 1.92 wt.% $SnO_2$, 18.4 wt.% $Fe_3O_4$
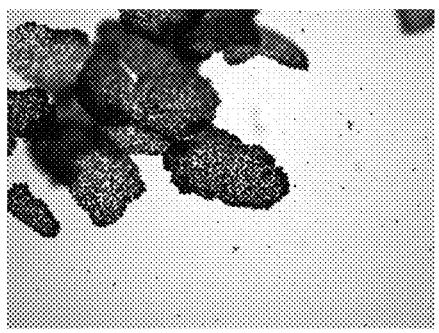
Figure 2 – 3.2 wt.% $SnO_2$, 31 wt.% $Fe_3O_4$
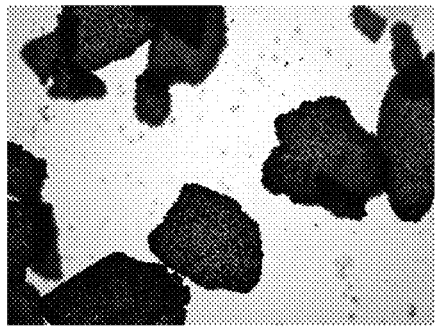
Figure 3 - 2.76 wt.% $SnO_2$, 40 wt.% $Fe_3O_4$ Effect of Tin Oxide Deposition on $Fe_3O_4$ Coverage
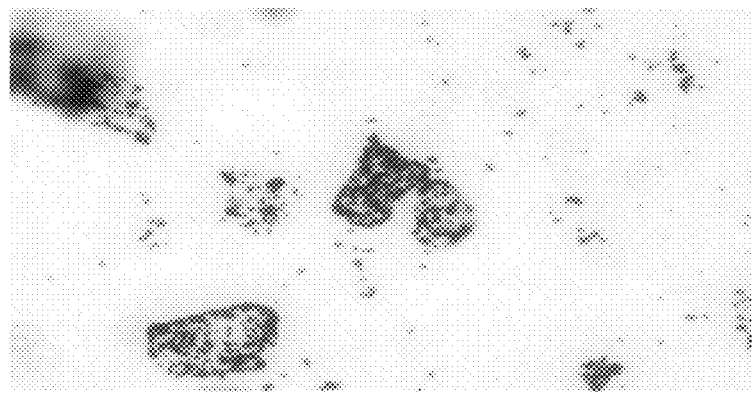
Figure 5 – No Tin Oxide, 25 wt. % $Fe_3O_5$

BLACK EFFECT PIGMENT

This application claims the benefit of U.S. Provisional Application No. 61/452,804 filed Mar. 15, 2011 herein incorporated entirely by reference.

BACKGROUND

Effect pigments, also known as pearlescent pigments or nacreous pigments, are used to impart a pearlescent luster, metallic luster and/or multi-color effect approaching iridescent, to a material. For instance, black effect pigments based on flake-form substrates are of particular interest in cosmetics. One of the primary black effect pigments approved for cosmetic applications includes $Fe_3O_4$-based effect pigments.

U.S. Pat. Nos. 3,926,659, 7,303,622 and U.S. publication no. 2007/0032573 disclose $Fe_3O_4$ based effect pigments.

$Fe_3O_4$-based effect pigments tend to be very stable and not subject to decomposition the way many color based pigments, such as carmine are. However, $Fe_3O_4$-based effect pigments normally do not provide sufficient blackness.

In addition, $Fe_3O_4$ does not bind well to platy substrates. For example, $Fe_3O_4$ adhesion to substrates such as mica and perlite is weak. Accordingly, once the $Fe_3O_4$ coated substrates are subjected to mechanical shear, such as hand mixing of the product in a lacquer, the $Fe_3O_4$ layer or coating is easily removed from the surface of the substrate. This removal of $Fe_3O_4$ coating or layer from the substrate can cause "staining" issues.

Thus, there is an on-going need in the art for black effect pigment compositions with improved darkness and improved adhesion to platy substrates.

SUMMARY

The inventors have discovered that some of these weaknesses in $Fe_3O_4$-based effect pigments, can be addressed by using the various embodiments disclosed herein.

The primary embodiments of this disclosure are directed to:

A novel black effect pigment

A paint, coating, printing ink, cosmetic formulation, laser marking, pigment composition or dry preparation, especially a cosmetic formulation comprising the inventive black effect pigment, A method of preparing said black effect pigment and A method of increasing the adhesion of $Fe_3O_4$ to a substrate.

Accordingly, the invention is directed to a black effect pigment comprising
 a) at least a partial layer of $SnO_2$ and/or hydrated $SnO_2$ on a substrate,
 b) at least a partial layer of $Fe_3O_4$
 c) and optionally, a further layer of metal oxide, wherein the partial layer of $Fe_3O_4$ may further contain ferric hydroxide and $Fe_2O_3$.

A paint, coating, printing ink, cosmetic formulation, laser marking, pigment composition or dry preparation, especially a cosmetic formulation comprising the inventive black effect pigment is an important embodiment of the present disclosure.

A method of preparing the black effect pigment comprises the steps of
 applying a coating or layer of $Fe_3O_4$ onto an at least partially coated or layered $SnO_2$ coated substrate and optionally applying a further metal oxide coating.

A method of increasing the adhesion of $Fe_3O_4$ to a substrate comprising the steps of
 a) at least partially coating the substrate with $SnO_2$ and/or $SnO_2$ hydrate,
 b) applying $Fe_3O_4$ to the at least partially coated substrate of step a) and
 c) optionally, applying a further metal oxide coating, wherein the partial layer of $Fe_3O_4$ may further contain ferric hydroxide and $Fe_2O_3$.

Alternatively, this may be expressed as a method of preparing a substrate surface for $Fe_3O_4$ deposition comprising the steps of
 a) at least partially coating the substrate with $SnO_2$ and/or $SnO_2$ hydrate,
 b) applying $Fe_3O_4$ to the at least partially coated substrate of step a) and
 c) optionally, applying a further metal oxide coating, wherein the partial layer of $Fe_3O_4$ may further contain ferric hydroxide and $Fe_2O$

BRIEF DESCRIPTION OF THE DRAWINGS

FIGS. 1 through 4 are representative of tin oxide treated mica upon which $Fe_3O_4$ is deposited. The black spots indicate $Fe_3O_4$. Pictures 1-4 were taken on a Nikon LV-100 at 400× magnification. Picture 5 was taken at 100× magnification.

FIG. 1 represents 0.39 wt. % $SnO_2$ and/or $SnO_2$ hydrate layer and 39 wt. % $Fe_3O_4$ layer on mica.

FIG. 2 represents 3.2 wt. % $SnO_2$ and/or $SnO_2$ hydrate layer and 31 wt. % $Fe_3O_4$ layer on mica.

FIG. 3 represents 2.6 wt. % $SnO_2$ and/or $SnO_2$ hydrate layer and 40 wt. % layer of $Fe_3O_4$ on mica.

FIG. 4 represents 1.92 wt. % $SnO_2$ and/or $SnO_2$ hydrate layer and 18.4 wt. % layer of $Fe_3O_4$ on mica.

FIG. 5 represents 25 wt. % layer of $Fe_3O_4$ on mica.

DETAILED DESCRIPTION

Definitions

The term "substrate" for purposes of this disclosure means platy inorganic or organic treated or untreated materials. For example, such platy materials may include aluminum oxide, platy glass, perlite, aluminum, natural mica, synthetic mica, bismuth oxychloride, platy iron oxide, platy graphite, platy silica, bronze, stainless steel, natural pearl, boron nitride, copper flake, copper alloy flake, zinc flake, zinc alloy flake, zinc oxide, enamel, china clay, porcelain, titanium oxide, platy titanium dioxide, titanium suboxide, kaolin, zeolites and combinations thereof.

As defined above the substrate may be treated or untreated. For example, the substrate may be treated with virtually any agent such silicones and coupling agents. Alternatively, the substrate may be mechanically treated to smooth the surface, or plasma or radiation treatments to activate the surface before application of the at least partial coatings of $SnO_2$ and $Fe_3O_4$.

In a preferred embodiment, the substrate may be selected from the group consisting of natural mica, synthetic mica, perlite, platy glass, bismuth oxychloride and aluminum. Mica (natural and synthetic) is of special importance.

The descriptor "platy" as used herein is well understood in the art. The term "platy" may be used interchangeably with flake, flake-like, plate-like, platelet and flaky.

When the term black is used this means substantially black. "Substantially black" means for purposes of this disclosure that the black color is distinguished by sufficient blackness, that is of low L value, and the "a" and "b" values are around the zero point. The black may contain overtones of other colors such as gold, red, green etc. Defined adjustments of the "a" and "b" values enables black interference pigments having a gold, green red or blue tint to be obtained.

The phrase "at least partial layers or coatings" refers to the $SnO_2$, $Fe_3O_4$ or optional metal oxide coating, layers or stacks and means that the coating may be incomplete or partial, that is not a completely continuous layer covering the total platy surface but only part of the platy surface.

The disclosures of each and every patent, patent application, and publication cited herein are hereby incorporated herein by reference in their entirety.

Substrate

As described above, the platy substrate may be organic or inorganic but is preferably inorganic.

The substrate may be further characterized in a number of ways. For example, the platy substrate diameter may range from about 0.1 to about 350 microns, preferably about 5 to about 250 microns and most preferably from about 1 to about 150 microns.

The platy substrate may also be a mixture of identical or different substrates, each having different particle sizes. The substrate mixture can consist of two, three or more different substrates. Preference is given to one substrate, say for example natural mica or synthetic mica.

$SnO_2$

In an important embodiment, the $SnO_2$ and/or hydrated $SnO_2$ may partially or completely coat the substrate wherein the partially coated or completely coated substrate is adjacently and directly coated with at least a partial coating or layer of $Fe_3O_4$.

The $SnO_2$ coating or layer may or may not directly impinge on the substrate. However, the $SnO_2$ coating or layer will directly contact at least one $Fe_3O_4$ layer, stack or coating.

Another important embodiment is the platy substrate, especially mica may be seeded with $SnO_2$ followed by or with an adjacent $TiO_2$ layer. Accordingly a $TiO_2$ layer containing $SnO_2$ may be used as the adjacent layer upon which the $Fe_3O_4$ coating is applied.

It is preferably however, that the $SnO_2$ coating or layer which impinges on the $Fe_3O_4$ coating layer is not incorporated into a $TiO_2$ coating or layer.

The amount of the $SnO_2$ or hydrated $SnO_2$ compound required to be deposited onto the platy surface can vary. But typically the minimum amount of tin oxide and/or hydrate thereof ranges from at least about 0.01 wt. %, preferably 0.1 wt. %, and most preferably about 0.5 wt. % $SnO_2$ and/or hydrate thereof based on the total weight of the effect pigment.

Accordingly, the amount of $SnO_2$ and/or $SnO_2$ hydrate as a wt. percent of the effect pigment ranges from at least 0.01 to 20 wt. %, preferably 0.1 to 10 wt. %, and most preferably 0.5 to 4 wt. % based on the total weight of the effect pigment.

One of the advantages of the present black effect pigment is the at least partial $SnO_2$ or at least partial hydrated $SnO_2$ coating onto the substrate, especially mica or synthetic mica, provides a much improved substrate surface for application of the adjacent $Fe_3O_4$ layer or coating. This results in a greater amount of the $Fe_3O_4$ adhering to the platy substrate rather than as $Fe_3O_4$ particle unassociated with the substrate. This gives a truer, deeper black effect pigment with little or no staining issues and an effect pigment which is effective at lower concentrations.

Various tin salts may be used as the source of the tin oxide and/or tin oxide hydrate compound and both stannous and stannic salts are applicable. It is characteristic of many tin salts that the solutions readily hydrolyze on dilution to form highly colloidal suspensions which are positively charged. Insolubilization of the nucleating surface of tin oxide compound is readily effected by the heat, either by drying the isolated flakes or by heating the slurry to relatively high temperatures.

$Fe_3O_4$

The magnetite layer or $Fe_3O_4$ layer can be deposited on a suitable platy substrate either directly by wet chemical method, Chemical Vapor Deposition (CVD), Physical Vapor Deposition (PVD). Alternatively, the platy substrate can first be coated with iron(III) oxide which is subsequently reduced to a layer containing iron(II) oxide.

It is important to note that when $Fe_3O_4$ forms or deposits onto the substrate, small amounts of ferric hydroxide and $Fe_2O_3$ form and will likely also be present.

Typically the $Fe_3O_4$ coating ranges from about 20 to about 70 wt. %, preferably about 25 to about 65 wt. %, about 35 to about 60 wt. % of the total weight of the inventive black effect pigment.

The $SnO_2$ and/or hydrated $SnO_2$ layer(s) and/or the $Fe_3O_4$ layer(s) may encapsulate or form a continuous coating(s) or layer(s) on the substrate. It is not necessary that the tin oxide and iron oxide coatings be partial.

Metal Oxide Coating

Another embodiment of the invention is the adherence of the $Fe_3O_4$ on the surface of the substrate may be further improved using an additional metal oxide coating. This coating may function as an outer protective layer for the inner $Fe_3O_4$ layer or layers protecting the $Fe_3O_4$ layers from removal upon shear. This further metal oxide coating may also protect the $Fe_3O_4$ from further oxidation.

Additionally the metal oxide layer evens the underlying $Fe_3O_4$ layer(s) making the effect pigment more suited to skin and cosmetic applications.

This optional protective layer may be selected from virtually any metal oxide, preferably a transparent metal oxide. For example, metal oxides such as $SiO_2$, $TiO_2$, $ZrO_2$, $Al_2O_3$ and $ZnO_2$ are envisioned.

A preferred embodiment for the optional metal oxide layer c) is a metal oxide selected from the group consisting of $SiO_2$, $TiO_2$ and $ZnO_2$, especially $SiO_2$ and $TiO_2$ and most especially $SiO_2$.

This optional protective layer or metal oxide outer layer may range from about 1 nm to about 350 nm, preferably about 5 nm to about 100 nm and especially 10 to about 100 nm.

Although the embodiments discussed so far are the three layers, a) the $SnO_2$ or hydrated $SnO_2$ layer or coating, b) the $Fe_3O_4$ layer or coating and c) the metal oxide layer, the inventive black effect pigment is not limited to these three layers. Other variations are possible. For example interference pigments of the following layer sequences are envisioned but not limited to:

substrate/$SnO_2$ and/or $SnO_2$ hydrate+$Fe_3O_4$ (in same layer)

substrate/$SnO_2$ and/or $SnO_2$ hydrate+$Fe_3O_4$ (in same layer)/$SiO_2$ substrate/$SnO_2$ and/or $SnO_2$ hydrate/$Fe_3O_4$ substrate/$SnO_2$ and/or $SnO_2$ hydrate/$Fe_3O_4$/$SiO_2$ substrate/$SnO_2$ and/or $SnO_2$ hydrate/$Fe_3O_4$/$TiO_2$ substrate/$SnO_2$ and/or $SnO_2$ hydrate/$Fe_3O_4$/$ZnO_2$ substrate/$SnO_2$ and/or $SnO_2$ hydrate/$Fe_3O_4$/$ZrO_2$ substrate/$TiO_2$+$SnO_2$/$Fe_3O_4$/$SiO_2$ substrate/$SnO_2$ and/or $SnO_2$ hydrate/$TiO_2$+$SnO_2$/$Fe_3O_4$/$SiO_2$ substrate/$TiO_2$+$SnO_2$/$SnO_2$ and/or $SnO_2$ hydrate/$Fe_3O_4$/$SiO_2$ substrate/$SnO_2$ and/or $SnO_2$ hydrate/$Fe_3O_4$/$TiO_2$+$SnO_2$/$Fe_3O_4$/$SiO_2$ substrate/$SnO_2$ and/or SnO2 hydrate/$Fe_3O_4$/$SiO_2$/$SnO_2$/$Fe_3O_4$/$SiO_2$ substrate/$SiO_2$/$SnO_2$ and/or $SnO_2$ hydrate/$Fe_3O_4$/$TiO_2$ substrate/$SnO_2$/$TiO_2$/$SnO_2$/$Fe_3O_4$/$SiO_2$ As indicated above, the inventive black pigment also embodies $SnO_2$ and $Fe_3O_4$ present in one layer or the $SnO_2$ and $Fe_3O_4$ present in two separate layers.

Preparation of the Black Effect Pigment

An effect pigment useful in the claimed pigment composition can be formed by any process known in the art. It can be accomplished, as one example, by precipitating a metal oxide onto laminar platy substrate particulate and thereafter calcining the coated particulates to provide metal oxide-coated flake-form pigment.

In general, the procedure for preparing effect pigments involves dispersing the substrate, especially a platy substrate and combining that dispersion with a precursor, which results in the deposition of an oxide of the precursor onto the substrate. For instance, in the case of titanium oxide, titanyl chloride or titanium tetrachloride can be used as the precursors. In the case of iron oxide, the precursor source material can be ferrous sulfate and in the case of tin oxide and/or hydrates thereof the precursor can be $SnCl_2$. The pH of the resulting slurry is maintained at an appropriate level during the addition of the iron salts by the use of a suitable base such as sodium hydroxide in order to cause precipitation of the iron oxide(s) on to the platy substrate. If desired, additional layers of titanium oxide, silicon oxide, $SnO_2$ and Iron oxide (or other metals) can be deposited sequentially.

Other coating procedures, such as for example, chemical vapor deposition (CVD) or physical vapor deposition processes (PVD), can also be used to prepare effect pigments useful in the claimed composition.

Accordingly the method of preparing the substantially black effect pigment comprises the steps of applying a coating or layer of $Fe_3O_4$ onto an at least partially coated or layered $SnO_2$ or hydrated $SnO_2$ coated substrate and optionally applying a further metal oxide coating.

Wet chemical methods are of particular importance. The substrate is normally suspended or dispersed in a liquid, especially water with one or more hydrolysable metal salts being added at a pH which is suitable for hydrolysis. The pH is selected in such a way that the metal oxides or metal oxide hydrates are precipitated directly onto the flakes without secondary precipitations occurring. The pH can be kept constant by simultaneous metering-in of a base of acid.

In the case of the inventive black effect pigment, the $SnO_2$ and/or $SnO_2$ hydrate treated platy substrate may be dispersed in a liquid in the presence of a hydrolysable iron salt such as $FeSO_4$ at a basic pH with or without reducing conditions.

The precipitation of $SnO_2$ and/or $SnO_2$ hydrates onto the platy substrate may be carried out separately with drying or calcination followed by formation of a $Fe_3O_4$ layer. Alternatively, the tin oxide and/or hydrates thereof coating may be applied under acidic conditions in a first step without drying or calcination followed by deposition of the $Fe_3O_4$ under basic reducing or non-reducing conditions.

The invention is directed also to a novel method or use of improving the adhesion of $Fe_3O_4$ to a platy substrate, for example mica or synthetic mica.

The method entails increasing the adhesion of $Fe_3O_4$ to a substrate comprising the steps of a) at least partially coating the substrate, especially mica (synthetic or natural), with $SnO_2$ and/or hydrated $SnO_2$
b) applying $Fe_3O_4$ to the at least partially coated substrate of step a) and c) optionally, applying a further metal oxide coating, wherein the partial layer of $Fe_3O_4$ may further contain ferric hydroxide and $Fe_2O_3$.

The inventive black effect pigment may be further coated to give the effect pigment a hydrophobic or hydrophilic character. Such treatment may improve formulation compatibility or improve the feel or touch of the pigments on skin. For example, U.S. published application no. 2008/0213322 describes the coating of effect pigments with cetydimethicone to increase the hydrophobicity of the pigment. Other examples of hydrophobic treatment would include treatment of the pigment with cyclotetradimethylsiloxane, cyclopentadimethylsiloxane, cyclohexadimethylsiloxane, cyclocopolymer of dimethylsiloxane/methyloctylsiloxane, hexylheptamethyltrisiloxane, lauroyl lysine and octylheptamethyltrisiloxane to name just a few of the possible coating agents.

Applications of the Inventive Black Effect Pigment

The effect pigments according to the invention can be used for all customary purposes, for example for coloring polymers in the mass, coatings (including effect finishes, including those for the automotive sector) and printing inks (including offset printing, intaglio printing, gravure, bronzing and flexographic printing), and also for applications in cosmetics, in ink-jet-printing, for dyeing textiles, as well as laser marking of papers and plastics. Such applications are known from reference works, for example "Industrielle Organische Pigmente" (W. Herbst and K. Hunger, VCH Verlagsgesellschaft mbH, Weinheim/New York, $2^{nd}$, completely revised edition, 1995).

A paint, coating, printing ink, plastic, cosmetic formulation, laser marking, pigment composition or dry preparation, especially a cosmetic formulation comprising the inventive black effect pigment are important embodiments of the present disclosure.

In one embodiment, the composition is part of a cosmetic composition. The form of the cosmetic composition can be any form normally used for cosmetics such as cream, emulsion, foam, gel, lotion, milk, mousse, ointment, paste, powder, spray, or suspension. The cosmetic composition can be any colored cosmetic used on the skin, hair, eyes, or lips, such as concealing sticks, foundation, stage make-up, mascara (cake or cream), eye shadow (liquid, pomade, powder, stick, pressed or cream), hair color, lipsticks, lip gloss, kohl pencils, eye liners, blushers, eyebrow pencils, and cream powders. Other exemplary cosmetic compositions include, but are not limited to, nail enamel, skin glosser stick, hair sprays, face powder, leg-makeup, insect repellent lotion, nail enamel remover, perfume lotion, and shampoos of all types (gel or liquid). In addition, the claimed compositions can be used in shaving cream (concentrate for aerosol, brushless, lathering), hair groom, cologne stick, cologne, cologne emollient, bubble bath, body lotion (moisturizing, cleansing, analgesic, astringent), after shave lotion, after bath milk and sunscreen lotion. For a review of cosmetic applications, see Cosmetics: Science and Technology, 2nd Ed., Eds: M. S. Balsam and Edward Sagarin, Wiley-Interscience (1972) and deNavarre, The Chemistry and Science of Cosmetics, 2nd Ed., Vols 1 and 2 (1962), Van Nostrand Co. Inc., Vols 3 and 4 (1975), Continental Press, both of which are hereby incorporated by reference.

The cosmetic composition optionally comprises at least one cosmetically acceptable auxiliary agent. Cosmetically acceptable auxiliary agents include, but are not limited to, carriers, excipients, emulsifiers, surfactants, preservatives, fragrances, perfume oils, thickeners, polymers, gel formers, dyes, absorption pigments, photo protective agents, consistency regulators, antioxidants, antifoams, antistats, resins, solvents, solubility promoters, neutralizing agents, stabilizers, sterilizing agents, propellants, drying agents, opacifiers, cosmetically active ingredients, hair polymers, hair and skin conditioners, graft polymers, water-soluble or dispersible silicone-containing polymers, bleaches, care agents, colorants, tinting agents, tanning agents, humectants, refatting agents, collagen, protein hydrolyzates, lipids, emollients and softeners, tinting agents, tanning agents, bleaches, keratin-hardening substances, antimicrobial active ingredients, photofilter active ingredients, repellant active ingredients, hyperemic substances, keratolytic and keratoplastic substances, antidandruff active ingredients, antiphlogistics, keratinizing substances, active ingredients which act as antioxidants and/or as free-radical scavengers, skin moisturizing or humectants substances, refatting active ingredients, deodorizing active ingredients, sebostatic active ingredients, plant extracts, antierythematous or antiallergic active ingredients and mixtures thereof. Cosmetic formulations are known in the art. See, for instance, US Publication Nos. 20080196847 and 20100322981.

The inventive black effect pigment may be added in any tinctorially effective amount to the paint, coating, printing ink, high molecular weight organic material, cosmetic formulation, laser marking, pigment composition or dry preparation.

The black effect pigment may be added to such materials as paint, coating, printing ink, high molecular weight organic material, cosmetic formulation, laser marking, pigment composition or dry preparation at concentrations ranging for 0.0001 to about 90 wt. %, for example about 0.001 to about 80 wt. %, especially 0.01 to about 50 wt. % wherein the wt. % is based on the total weight of the material.

In regard to cosmetic formulations the inventive black effect pigment may be added from about 0.0001 to 90 wt. % based on the total weight of the cosmetic formulation. The cosmetic formulation most likely will further contains a cosmetically suitable carrier material ranging from about 10 to about 90 wt. %. The cosmetically suitable carrier material is preferably different than water.

EXAMPLES

The compositions and methods of use are further described in detail by reference to the following experimental examples. These examples are provided for purposes of illustration only, and are not intended to be limiting unless otherwise specified. Thus, the compositions and methods of use should in no way be construed as being limited to the following examples, but rather, should be construed to encompass any and all variations which become evident as a result of the teaching provided herein.

Example 1

100 g of natural mica is slurried in 1000 ml of distilled water in a 3 l L flask. Slurry is stirred to keep homogeneous and heated to 82° C. The pH is adjusted to 1.4 with HCl. $SnCl_4$ is added at controlled rate and the pH is held at 1.4 with NaOH. After addition, stirring is continued 30-60 minutes. Slurry can be cooled, filtered, washed and calcined, then reslurried in 1000 ml distilled water. The slurry is again stirred and heated to 85° C., pH adjusted to 8.2, and $NaNO_3$ is added. $N_2$ is bubbled through the slurry to purge oxygen. $FeSO_4$ (acidified) solution is pumped in at controlled rate. The pH is controlled at 8.2 with NaOH. A sample is removed, vacuum filtered, washed, dried and evaluated.

Example 2

100 g of synthetic mica is slurried in 1000 ml of distilled water in a 3 l L flask. Slurry is stirred to keep homogeneous. The pH is adjusted to 1.6 with HCl. $SnCl_4$ is added at controlled rate and the pH is held at 1.6 with NaOH. After addition, stirring is continued 30-60 minutes. The slurry is heated to 85° C., pH adjusted to 8.2, $N_2$ is bubbled through the slurry and $NaNO_3$ is added. $FeSO_4$ (acidified) solution is pumped in at controlled rate. The pH is controlled at 8.2 with NaOH. A sample is removed, vacuum filtered, washed, dried and evaluated.

Example 3

100 g of synthetic mica is slurried in 1000 ml of distilled water in a 3 l L flask. Slurry is stirred to keep homogeneous and heated to 85° C. The pH is adjusted to 1.6 with HCl. $SnCl_4$ is added at controlled rate and the pH is held at 1.6 with NaOH. After addition, stirring is continued 30-60 minutes. The slurry is cooled, filtered, rinsed and calcined. The powder is reslurried, stirred, heated to 85° C., pH adjusted to 8.2, $N_2$ is bubbled and $NaNO_3$ is added. $FeSO_4$ (acidified) solution is pumped in at controlled rate. The pH is controlled at 8.2 with NaOH. A sample is removed, vacuum filtered, washed, dried and evaluated. To encapsulate the $Fe3O_4$ to the surface, a metal oxide layer can be deposited over the $Fe_3O_4$. 20% sodium meta silicate can be added at pH 8.0, temperature of 72° C. and pH balanced with HCl, or $TiOCl_2$ can be added at pH 1.4-2.2 and pH balanced with NaOH to form $TiO_2$.

Example 4

100 g of natural mica is slurried in 1000 ml of distilled water in a 3 l L flask. Slurry is stirred to keep homogeneous and heated to 82° C. The pH is adjusted to 1.4 with HCl. $SnCl_4$ is added at controlled rate and the pH is held at 1.4 with NaOH. after addition, stirring is continued 30-60 minutes. The slurry is heated to 85° C., pH adjusted to 8.2, $NaNO_3$ is added, and then $FeSO_4$ (acidified) solution is pumped in. The pH is controlled at 8.2 with NaOH. A sample is removed, vacuum filtered, washed, dried and evaluated. To encapsulate the $Fe_3O_4$ to the surface, a metal oxide layer can be deposited over the $Fe_3O_4$. 20% sodium metal silicate can be added at pH 8.0, temperature of 72° C. and pH balanced with HCl, or $TiOCl_2$ can be added at pH 1.4-2.2 and pH balanced with NaOH.

Example 5

Comparative 100 g of natural mica is slurried in 1000 ml of distilled water in a 3 l L flask. The slurry is heated to 85° C., pH adjusted to 8.2, $NaNO_3$ is added, and then $FeSO_4$ (acidified) solution is pumped in. The pH is controlled at 8.2 with NaOH. A sample is removed, vacuum filtered, washed, dried and evaluated.

Example 6

100 g of perlite is slurried in 1000 ml of distilled water in a 3 l L flask. Slurry is stirred to keep homogeneous and heated to 82° C. The pH is adjusted to 1.4 with HCl. $SnCl_4$ is added at controlled rate and the pH is held at 1.4 with NaOH. After addition, stirring is continued 30-60 minutes. Slurry can be cooled, filtered, washed and calcined, then reslurried in 1000 ml distilled water. The slurry is again stirred and heated to 85° C., pH adjusted to 8.2, and $NaNO_3$ is added. $N_2$ is bubbled through the slurry to purge oxygen. $FeSO_4$ (acidified) solution is pumped in at controlled rate. The pH is controlled at 8.2 with NaOH. A sample is removed, vacuum filtered, washed, dried and evaluated.

TABLE I

Color measurements carried out on a X-Rite MA68II.

| | Black | | | White | | | Particle Size | | | % FeSO4 | SnO2 |
|---|---|---|---|---|---|---|---|---|---|---|---|
| Example | L | C | H | L | C | h | $D_{10}$ | $D_{50}$ | $D_{90}$ | wt. % | wt. % |
| 1 | 36.09 | 1.62 | 275.69 | 44.81 | 0.91 | 288.64 | 9.893 | 20.683 | 38.88 | | |
| 2 | 36.4 | 4.63 | 267.52 | 36.46 | 4.23 | 269.59 | 21.16 | 44.193 | 85.295 | | |
| 3[1] | 40.54 | 2.16 | 272.66 | 43.09 | 1.96 | 270.88 | 32.796 | 66.129 | 120.522 | | |
| 4[2] | 48.42 | 1.44 | 290.33 | 54.84 | 1.13 | 292.47 | 22.725 | 48.553 | 92.353 | 37.46 | 1.78 |
| 4a[3] | 38.85 | 4.65 | 277.06 | 46.36 | 3.18 | 275.61 | 36.085 | 73.153 | 133.432 | | |
| 5 | 31.42 | 2.18 | 274.75 | 37.06 | 0.95 | 330.17 | 8.804 | 19.429 | 37.486 | | |

[1] Example 3 is substrate/$SnO_2$/$Fe_3O_4$/$SiO_2$
[2] Example 4 is substrate/$SnO_2$/$Fe_3O_4$/$SiO_2$
[3] Example 4a is substrate/$SnO_2$/$Fe_3O_4$/$TiO_2$

Application Examples

Pressed Eye Shadow Powder and Nail Enamel Drawdowns

Composition of Pressed Eye Shadow Powder

| Ingredients | Weight Fraction (%) |
|---|---|
| Pressed Powder Base | 59% |
| Liquid binder | 6.00 |
| Black Pigment compositions[1] a-d | 35.00 |

Composition of Nail Enamel Drawdowns

| Phase | Ingredient | % w/w |
|---|---|---|
| A | Nail Enamel Base | 94.00 |
| | UV absorbers | q.s. |
| B | Pigment | 6.0 |

Procedure

Add phase A in an appropriate size vessel fitted with a propeller mixer. Add Phase B to Phase A mixing until batch is uniform.

Samples of Black Pigment Compositions a) Inventive Black from Example 1 and 2 (mica/SnO2/~38 wt. % Fe3O4)-(JAS-0287-1). Synthetic mica (D10 is 20.77 microns, D50 is 44.84 microns, D90 is 81.45 microns)
b) Commercial Black Mica (mica/$TiO_2$/47-53% $Fe_3O_4$). (CLE-100052A)
c) Inventive Black but using Perlite as substrate (pearlite/$SnO_2$/~55% $Fe_3O_4$) (JAS-0286-1) The particle size distribution for the perlite is D10 is 8.50, D50 is 24.32 and D90 is 52.68.
d) Synthetic Mica analog (CLM-100050A) is a mixture of 62 wt. % synthetic mica and 38 wt. % $Fe_3O_4$. The synthetic mica particle distribution is the same as a).
e) Inventive black pigment from synthetic mica/48% $Fe_3O_4$/$SiO_2$
f) Inventive black pigment from natural mica/48% $Fe_3O_4$/$SiO_2$ Results Pressed Eye Shadow Powder Results and Nail Enamel Drawdowns Inventive Blacks a) (JAS-0287-1), a), c), e) and f) when incorporated into either the pressed powder or the nail drawdown deliver a darker/stronger color in comparison to b) and d). This is quite surprising in regard to b) as the Commercial Black Mica contain more wt. % $Fe_3O_4$. When d) is viewed side by side with the inventive black a), the inventive a) is also darker. Furthermore, the inventive blacks show better dispersibility when compared to analog d).

Additional Formulations Containing the Inventive Black

| | Body Splash | |
|---|---|---|
| Phase | Ingredients | % w/w |
| A | DI Water | 28.70 |
| | Disodium EDTA | 0.02 |
| | Acrylates/C10-30 Alkyl Acrylate Crosspolymer (CARBOPOL ETD 2020)[1] (2% aqueous dispersion) | 10.00 |
| | 2-Amino 2-Methyl Propanol (amp-95)[2] | 0.10 |
| | Glycerin (and) Glyceryl Polyacrylate (HISPAGEL Oil, Low Viscosity)[3] | 2.00 |
| B | Fragrance | q.s |
| | Polysorbate 20 (and)PEG 40 Castor Oil | 1.00 |
| | Glycereth-26 (PROTACHEM GL-26)[4] | 1.00 |
| | Methylpropanediol (MP Diol Glycol)[5] | 2.00 |
| C | Alcohol (SD 39C) | 55.00 |
| | Reflecks ™ Pinpoints of Pearl G130L(Calcium SodiumBorosilicate (and) $TiO_2$) | 0.12 |
| | Chione ™ Snowfall White S130D(Synthetic Fluorphlogopite (and)$TiO_2$)[6] | 0.01 |
| | Inventive Black from examples 1, 3, 4 and/or 6 (Mica/SnO2/Fe3O4, (Mica/$SnO_2$/$Fe_3O_4$/ $SiO_2$, Mica/$SnO_2$/$Fe_3O_4$/$TiO_2$, perlite/$SnO_2$/$Fe_3O_4$/$SiO_2$) | 0.05 |

-continued

| | Procedure | |
|---|---|---|
| | I. Add ingredients from Phase A in the order listed to the water at room temperature with moderate agitation And mix until uniform. Avoid aeration. | |
| | II. Pre-mix Phase B-C separately at room temperature. Combine Phase B-C and add to Phase A with moderate agitation. Mix until uniform. Avoid aeration. | |
| | Suppliers and Trademark Owners | |
| | 1. The Lubrizol Corporation | 4. Protameen Chemicals Inc. |
| | 2. Dow Chemical Company | 5. Lyondell Chemical Company |
| | 3. Hispano Quimica S.A./Centerchem, Inc | 6. BASF |

Concealer Stick

| Phase | Ingredients | % w/w |
|---|---|---|
| A | Beeswax (WHITE BEESWAX)[1] | 9.00 |
| | Hydrogenated Olive Oil/*Olea Europaea* (Olive) Fruit Oil Unsaponifiables (OLIWAX)[2] | 12.00 |
| | *Copernicia Cerifera* Wax (CARNAUBA T-3)[1] | 3.00 |
| | *Crambe Abyssinica* Seed Oil and Shea Butter extract (FANCOR ABYSEA)[3] | 15.00 |
| | Meadowfoam Estolide (FANCOR MEADOWESTOLIDE)[3] | 3.00 |
| | *Prunus Amygdalus Dulcis* Seed Oil (SWEET ALMOND OIL)[4] | 12.00 |
| | *Ricinus Communis*/Seed Oil(CASTOR OIL)[5] | 6.00 |
| | Luvitol ® Lite (Hydrogenated Polyisobutene)[6] | 10.00 |
| B | *Crambe Abyssinica* Seed Oil (FANCOR ABYSSINIAN OIL)[3] | 10.00 |
| | Chroma-Lite ® Mauve CL4511 (Mica/Bismuth Oxychloride/Iron Oxides)[6] | 7.00 |
| | Inventive Black from examples 1, 3, 4 and/or 6 (Mica/SnO2/Fe3O4, (Mica/SnO$_2$/Fe$_3$O$_4$/SiO$_2$, Mica/SnO$_2$/Fe$_3$O$_4$/TiO$_2$, perlite/SnO$_2$/Fe$_3$O$_4$/SiO$_2$) | 3.00 |
| | Chione ™ Snowfall White S130D (Synthetic Fluorphlogopite/TiO$_2$)[6] | 5.00 |
| | Desert Reflections ® Canyon Sunset 332D(Mica/TiO$_2$/iron Oxides) [6] | 5.00 |
| | Antioxidants | q.s. |
| | Preservatives | q.s. |
| | Procedure | |
| | I. Pre-disperse Phase B | |
| | II. Weigh all Phase A ingredients in a vessel and heat to 85 ± 3° C., stirring until melted and uniform. | |
| | III. Add premixed Phase B to Phase A, maintaining temperature at 82 ± 3° C. for 30 minutes with gentle agitation(This will allow de-aeration if vacuum is not available). | |
| | IV. Reduce temperature to 75 ± 3° C. | |
| | V. Pour into molds. | |
| | Suppliers and Trademark Owners | |
| | 1. Koster Keunen, LLC | 4. Jeen International Corporation |
| | 2. B&T Company | 5. Alzo International Inc. |
| | 3. Fancor Ltd. | 6. BASF |

Cream Foundation

| Phase | Ingredients | % w/w |
|---|---|---|
| A | DI Water (q.s to 100%) | 47.94 |
| | Methylpropanediol (mpdiol Glycol)[1] | 5.00 |
| | Magnesium Aluminum Silicate (VEEGUM)[2] | 0.60 |
| | Xanthan Gum (KELTROL CG-T)[3] | 0.40 |
| B | Cetearyl Olivate/Sorbitan Olivate (OLIVEM 1000)[4] | 4.00 |
| | Hydrogenated Olive Oil/*Olea Europaea* (Olive) Fruit Oil/*Olea Europaea* (Olive) Oil Unsaponifiables (OLIWAX)[4] | 2.00 |
| | Caprylic/Capric Triglyceride/Di-PPG-3 Myristyl Ether Adipate/Sorbitan Isostearate | 7.00 |
| | Meadowfoam Estolide/Meadowfoam Delta-Lactone(MEADOWDERM 100)[6] | 2.00 |
| | Isodecyl Neopentanoate (CERAPHYL SLK)[7] | 5.00 |
| | Antioxidants | q.s. |
| | Preservatives | q.s. |
| C | Kaolin (HUBER 90)[8] | 0.50 |
| | Polymethyl Methacrylate (PMMA H)[9] | 4.00 |
| | Titanium Dioxide | 3.14 |
| | Mearlmica ® SVA(Mica/Lauroyl Lysine)[10] | 3.00 |
| | Inventive Black from examples 1, 3, 4 and/or 6 (Mica/SnO2/Fe3O4, (Mica/SnO$_2$/Fe$_3$O$_4$/SiO$_2$, Mica/SnO$_2$/Fe$_3$O$_4$/TiO$_2$, perlite/SnO$_2$/Fe$_3$O$_4$/SiO$_2$) | 0.12 |
| D | DI Water | 10.00 |
| | MultiReflections ™ Sunflower Sparkle 380P(Mica/TiO$_2$/SiO$_2$)[10] | 3.00 |
| | Cloisonné ® Satin Rouge 450M (Mica/TiO$_2$/Iron oxides)[10] | 2.30 |
| | Procedure | |
| | I. Add DI Water and MPDIOL Glycol to main vessel and begin homogenization. | |
| | II. Sprinkle in VEEGUM and homogenize until uniform. | |
| | III. Sprinkle in the KELTROL CG-T and homogenize until uniform. | |
| | IV. In a separate container, heat Phase B to 60-70° C. and mix until uniform. | |
| | V. Under homogenization add Phase B to Phase A at 70° C. | |
| | VI. Pulverize Phase C in appropriate blending equipment. | |
| | VII. Under homogenization, sprinkle Phase C to Phase AB until uniform color is achieved. Then, sweep mix. | |

-continued

|   | VIII. | Premix Phase D and add to Phase ABC and begin cooling batch. | | | |
|---|---|---|---|---|---|
|   | IX. | Drop batch at 40° C. | | | |
|   | Suppliers and Trademark Owners | | | | |
|   | 1. | Lyondell Chemical Company | 6. | Fancor Ltd. | |
|   | 2. | RT Vanderbilt, Inc. | 7. | ISP | |
|   | 3. | CP Kelco | 8. | J.M. Huber Corporation | |
|   | 4. | B&T Company | 9. | Brenntag Specialties, Inc. | |
|   | 5. | CRODA | 10. | BASF | |

Deodorant Stick

| Phase | Ingredients | % w/w |
|---|---|---|
| A | DI Water (q.s. to 100%) | 18.60 |
|   | Propylene Glycol | 59.20 |
|   | PEG-200 Hydrogenated Castor Oil/IPDI Copolymer (POLYDERM PPI-CO-200)[1] | 12.00 |
|   | Sodium Stearate (JEECHEM Sodium Stearate)[2] | 8.00 |
|   | Isosteareth-2 (HETOXOL IS-2)[3] | 2.00 |
|   | UV Absorbers | q.s. |
| B | Inventive Black from examples 1, 3, 4 and/or 6 (Mica/SnO2/Fe3O4, (Mica/SnO$_2$/Fe$_3$O$_4$/SiO$_2$, Mica/SnO$_2$/Fe$_3$O$_4$/TiO$_2$, perlite/SnO$_2$/Fe$_3$O$_4$/SiO$_2$) | 0.10 |
|   | Cellini ® Green 820CGBYF (Mica/TiO2 + Blue 1 Lake + Yellow 5 Lake + Hydrogenated Polyisobutene + Palmitic Acid [4] | 0.10 |
| C | Fragrance | q.s |
|   | Procedure | |
|   | I. Mix Propylene Glycol and water and heat to 80-85o C. | |
|   | II. Add Polyderm in small increments until all is melted and dissolved. | |
|   | III. Add Sodium Stearate and maintain temperature at 85o C. until solution is clear. | |
|   | IV. Add Isosteareth-2 Alcohol and mix well. | |
|   | V. Pre-disperse Phase B and add to Phase A. | |
|   | VI. Add Phase C to Phase A-B and mix until uniform. | |
|   | VII. Fill into appropriate containers | |
|   | Suppliers and Trademark Owners | |
|   | 1. Alzo International Inc.      3. Global Seven Inc. | |
|   | 2. Jeen International Corporation      4. BASF | |

Eyeliner

| Phase | Ingredients | % w/w |
|---|---|---|
| A. | DI Water (q.s to 100%) | 45.00 |
|   | Luviset ®Clear(VP/Methacrylamide/Vinyl Imidazole Copolymer) [1] | 20.00 |
|   | D-Panthenol 75W (Panthenol) [1] | 1.00 |
|   | Glycerin (and) Glyceryl Acrylate/Acrylic Acid Copolymer (and) Propylene Glycol (and) PVM/MA Copolymer (LUBRAJEL OIL) [2] | 10.00 |
|   | Antioxidants | q.s. |
|   | Preservatives | q.s. |
| B | Xanthan Gum (KELTROL CG-T) [3] | 1.50 |
| C | DI Water | 11.25 |
|   | Pearlescent and iridescent pigments | |
|   | Inventive Black from examples 1, 3, 4 and/or 6 (Mica/SnO2/Fe3O4, (Mica/SnO$_2$/Fe$_3$O$_4$/SiO$_2$, Mica/SnO$_2$/Fe$_3$O$_4$/TiO$_2$, perlite/SnO$_2$/Fe$_3$O$_4$/SiO$_2$) | 1.25 |
|   | Reflecks ™ Dimensions Shimmering Red G430Z (Calcium Sodium Borosilicate (and) Titanium Dioxide) [1] | 10.00 |
|   | Procedure | |
|   | I. In a suitable container add all Phase A ingredients. | |
|   | II. Sprinkle Phase B into Phase A while being rapidly agitated. | |
|   | III. Premix Phase C and add to Phase AB. | |
|   | *Note Cold process. | |
|   | Suppliers and Trademark Owners | |
|   | 1. BASF      3. CP Kelco | |
|   | 2. ISP | |

Hair Gloss

| Phase | Ingredients | % w/w |
|---|---|---|
| A | PEG-7 Glyceryl Cocoate (TEGOSOFT GC) [2] | 8.00 |
|   | Cremophor ® A 25 (Ceteareth-25) [1] | 22.00 |
|   | Cremophor ® WO 7 (PEG-7 Hydrogenated Castor Oil) [1] | 1.00 |
|   | Propylene Glycol | 3.00 |
|   | PEG-8 Methicone (MASIL SF 19 CG) [3] | 1.00 |
|   | Pearlescent and iridescent pigments | |
|   | Inventive Black from examples 1, 3, 4 and/or 6 (Mica/SnO2/Fe3O4, (Mica/SnO$_2$/Fe$_3$O$_4$/SiO$_2$, Mica/SnO$_2$/Fe$_3$O$_4$/TiO$_2$, perlite/SnO$_2$/Fe$_3$O$_4$/SiO$_2$) | 0.05 |

-continued

| | | |
|---|---|---|
| B | DI Water (q.s to 100%) | 64.85 |
| C | Fragrance (VERBENA MINT YY06-01079) [4] | 0.10 |
| | Preservatives | q.s. |

Procedure
I. Add Phase A ingredients in above order at 80° C. and mix until uniform. Assure each is dissolved prior to next addition.
II. Heat Phase B to 80° C. and combine with Phase A.
III. Cool to 50° C. while allowing air bubbles to rise out and foam to dissolve. Add fragrance and preservative.
IV. Pour into containers while liquid and allow to set at room temperature.

Suppliers and Trademark Owners
1. BASF
2. Evonik Goldschmidt GmbH
3. The Lubrizol Corporation
4. Ungerer & Company

Icy Gel Toothpaste

| Phase | Ingredients | % w/w |
|---|---|---|
| A | DI Water (q.s. to 100%) | 6.25 |
| | Sorbitol (LIPONIC 70-NC) [1] | 54.30 |
| | Glycerin | 10.00 |
| | Cellulose Gum | 0.50 |
| | PEG-32 (CARBOWAX PEG 1450) [2] | 3.00 |
| B | DI Water | 5.00 |
| | Sodium Benzoate | 0.30 |
| | Sodium Saccharin | 0.20 |
| C | Hydrated Silica (ZEODENT 165) [3] | 5.00 |
| | Hydrated Silica (ZEODENT 113) [3] | 15.00 |
| D | Flavor (Sweet Mint # 26037G) [4] | 0.15 |
| | Blue 1 (0.5% Aqueous Solution) | 0.10 |
| | Pearlescent and iridescent pigments | |
| | Inventive Black from examples 1, 3, 4 and/or 6 (Mica/SnO2/Fe3O4, (Mica/SnO$_2$/Fe$_3$O$_4$/SiO$_2$, Mica/SnO$_2$/Fe$_3$O$_4$/TiO$_2$, perlite/SnO$_2$/Fe$_3$O$_4$/SiO$_2$) | 0.20 |

Procedure
I. Pre-mix Water, Sorbitol and Glycerin, and disperse Cellulose Gum with mixing until thoroughly dispersed.
II. Add PEG-32 and heat to 50o C.
III. At 40o C. add pre-mixed Phase B to Phase A while mixing until completely uniform.
IV. Add Phase C to Phase A-B while under agitation.
V. Add Phase D ingredients one by one to Phase A-B-C mixing until completely uniform.
VI. Fill into appropriate containers Suppliers and Trademark Owners
1. Lipo Chemicals, Inc.
2. Dow Chemical Company
3. J.M Huber Corporation
4. Shaw Mudge & Company
5. BASF

Lip Balm

| Phase | Ingredients | % w/w |
|---|---|---|
| A | Pentaerythrityl Tetraisostearate (CRODAMOL PTIS) - (q.s to 100%) | 20.05 |
| | *Ricinus Communis* (Castor) Seed Oil | 11.60 |
| | Di-PPG-3 Myristyl Ether Adipate (CROMOLLIENT DP3A) [1] | 11.50 |
| | *Crambe Abyssinica* Seed Oil (FANCOR ABYSSINIAN OIL) [2] | 10.50 |
| | C10-30 Cholesterol/Lanosterol Esters (SUPER STEROL ESTER) [1] | 6.25 |
| | Meadowfoam Estolide (MEADOWESTOLIDE) 2 | 6.00 |
| | Meadowfoam Estolide (and) Meadowfoam Delta-Lactone (and) *Crambe Abyssinica* Seed Oil (and) *Carthamus Tinctorius* (Safflower) Seed Oil (and) Olive Oil Unsaponifiable (and) Beta-Sitosterol (ANTI-AGING SKIN COMPLEX) [2] | 5.00 |
| | *Euphorbia Cerifera* (Candelilla) Wax (Candelilla Wax SP 75) [3] | 8.00 |
| | *Copernicia Cerifera* (Carnauba) Wax (Carnauba Wax SP 63) [3] | 2.00 |
| | Ozokerite (Ozokerite Wax White SP 1026) [3] | 3.00 |
| | Microcrystalline Wax (MULTIWAX 180-W) [3] | 3.00 |
| | Antioxidants | q.s. |
| | Preservatives | q.s. |
| | Fragrance | q.s. |
| | Uvinul ® MC80 (Octinoxate) [4] | 5.00 |
| | Oxybenzone | 4.00 |
| B | Red 6* | 0.10 |
| | Pearlescent and iridescent pigments | |
| | Inventive Black from examples 1, 3, 4 and/or 6 (Mica/SnO2/Fe3O4, (Mica/SnO$_2$/Fe$_3$O$_4$/SiO$_2$, Mica/SnO$_2$/Fe$_3$O$_4$/TiO$_2$, perlite/SnO$_2$/Fe$_3$O$_4$/SiO$_2$) | 4.00 |

| | | |
|---|---|---|
| C | Fragrance | q.s |
| | Procedure | |
| | I. Weigh all of Phase A ingredients in a vessel and heat to 85 ± 3° C., stirring until melted and uniform. | |
| | II. Add premixed Phase B to Phase A maintaining temperature at 82 ± 3° C. for 30 minutes with gentle agitation. (This will allow de-aeration if vacuum is not available). | |
| | III. Cool to 75 ± 3° C. and add fragrance and pour into container. | |
| *Note: | If iron oxide or organic pigments are used, they should first be dispersed in *Ricinus Communis* (Castor) Seed Oil; this mixture should then be milled in either a colloid or roller mill. | |
| | Suppliers and Trademark Owners | |
| | 1. CRODA | 3. Strahl & Pitsch, Inc. |
| | 2. Fancor Ltd. | 4. BASF |

Lipstick

| Phase | Ingredients | % w/w |
|---|---|---|
| A | *Crambe Abyssinica* Seed Oil (FANCOR ABYSSINIAN OIL) [1] (q.s to 100%) | 34.86 |
| | *Euphorbia Cerifera* (Candelilla) Wax (Candelilla Wax SP 75) [2] | 3.00 |
| | *Copernicia Cerifera* (Carnauba) Wax (Carnauba Wax SP 63) [2] | 1.50 |
| | Beeswax (Beeswax White SP 422) [2] | 1.00 |
| | Ceresine (Ceresine Wax White SP 252) [2] | 6.00 |
| | Microcrystalline Wax (MULTIWAX 180-W) [2] | 1.50 |
| | Oleyl Alcohol (NOVOL) [3] | 3.00 |
| | Isosteryl Palmitate (JEECHEM ISP) [4] | 4.25 |
| | Caprylic/Capric Triglyceride | 8.25 |
| | Bis-Diglyceryl Polyacyladipate-2 (SOFTISAN 649) [5] | 2.00 |
| | Acetylated Lanolin Alcohol (JEELAN MOD) [4] | 2.50 |
| | Sorbitan Tristearate (JEECHEM STS) [4] | 1.75 |
| | Ozokerite (Ozokerite Wax White SP 1026) [2] | 6.75 |
| | Glyceryl Monolaurate (ULTRAPURE GML) [6] | 1.00 |
| | Antioxidants | q.s. |
| | Preservatives | q.s. |
| | UV Absorbers | q.s. |
| B | Meadowfoam Estolide (MEADOWESTOLIDE) [2] | 2.00 |
| | Red 6 Lake * | 3.14 |
| | Pentaerythrityl Tetraisostearate (CRODAMOL PTIS) [3] | 6.00 |
| | Chione ™ Snowfall White S130D (Synthetic Fluorphlogopite (and) Titanium Dioxide) [7] | 9.00 |
| | Pearlescent and iridescent pigments | |
| | Inventive Black from examples 1, 3, 4 and/or 6 (Mica/SnO2/Fe3O4, (Mica/SnO$_2$/Fe$_3$O$_4$/SiO$_2$, Mica/SnO$_2$/Fe$_3$O$_4$/TiO$_2$, perlite/SnO$_2$/Fe$_3$O$_4$/SiO$_2$) | 2.00 |
| C | Ethylhexyl Palmitate | 0.20 |
| | Biju ® Ultra UFC (Bismuth Oxychloride) [7] | 0.30 |
| D | Fragrance | q.s. |
| | Procedure | |
| | I. Weigh all of Phase A ingredients in a vessel and heat to 85 ± 3° C., stirring until melted and uniform. | |
| | II. Add premixed Phase B to Phase A, maintaining temperature at 82 ± 3° C. for 30 minutes with gentle agitation. | |
| | III. Pre-disperse Biju ® Ultra UFC in Ethylhexylpalmitate and add to Phase AB. | |
| | IV. Cool to 75 ± 3° C. and add fragrance. | |
| | V. Pour into container or components. | |
| *Note: | If iron oxide or organic pigments are used, they should first be dispersed in *Crambe Abyssinica* Seed Oil; this mixture should then be milled in either a colloid or roller mill. | |
| | Supplies and Trademark Owners | |
| | 1. Fancor Ltd. | 5. SASOL |
| | 2. Strahl & Pitsch, Inc. | 6. Ultra Chemical, Inc. |
| | 3. CRODA | 7. BASF |
| | 4. Jeen International Corporation | |

Eye Mascara

| Phase | Ingredients | % w/w |
|---|---|---|
| A | Caprylyl Methicone (DOW CORNING TORAY FZ-3196) [1] | 4.00 |
| | Lauryl PEG/PPG-18/18 Methicone (DOW CORNING 5200 FORMULATION AID) [1] | 6.00 |
| | *Copernicia Cerifera* (Carnauba) Wax (No. 1 Yellow Carnauba Wax) [2] | 3.00 |
| | C30-45 Alkyldimethylsilyl Polypropylsilsesquioxane (DOW CORNING SW-8005 C30 RESIN WAX) [1] | 2.00 |
| | Caprylic/Capric Triglyceride (JEECHEM CTG) [3] | 3.00 |
| | Uvinul ® A Plus B* (Ethylhexyl Methoxycinnamate (and) Diethylamino Hydroxybenzoyl Hexyl Benzoate) [4] | 0.10 |
| | Preservatives O/S | q.s. |
| | Vitamin E Acetate Care (Tocopheryl Acetate) [4] | 0.25 |
| B | Isododecane (Permethyl 99A) [5] (q.s to 100%) | 25.00 |
| | Isododecane (and) Disteardimonium Hectorite (and) Propylene Carbonate (BENTONE GEL ISD V) [6] | 6.00 |
| | Polymethyl Methacrylate (PMMA S) [7] | 5.00 |

| Phase | Ingredients | % w/w |
|---|---|---|
| C | Pearlescent and iridescent pigments | |
| | Inventive Black from examples 1, 3, 4 and/or 6 (Mica/SnO2/Fe3O4, (Mica/SnO$_2$/Fe$_3$O$_4$/SiO$_2$, Mica/SnO$_2$/Fe$_3$O$_4$/TiO$_2$, perlite/SnO$_2$/Fe$_3$O$_4$/SiO$_2$) | 2.00 |
| | Reflecks ™ Dimensions Luminous Gold G230M (Calcium Sodium Borosilicate (and) Titanium Dioxide) [4] | 4.00 |
| | DI Water | 17.65 |
| | Propylene Glycol | 2.00 |
| | Preservatives W/S | q.s. |
| D | Luviset ® Shape (Polyacrylate-22) [4] | 20.00 |
| | Procedure | |
| | I. In main vessel heat Phase A ingredients to 60° C. with continuous mixing. | |
| | II. In a side vessel premix Phase B into Phase A maintaining temperature to 60° C. | |
| | ** Note: Black 2 should first be dispersed in Isododecane; this mixture should then be milled in either a colloid or roller mill. | |
| | III. In a side vessel premix Phase C and heat to 50° C. | |
| | IV. Add Phase C to Phase AB under homogenization. Sweep mix and reduce heat to 50° C. | |
| | V. Add Phase D to Phase ABC. | |
| | VI. Package into appropriate containers. | |
| | * Uvinul ® A Plus B is not an approved Sunscreen active in the USA & Canada. | |
| | ** When Carbon Black pigments are used, they should first be dispersed in Isododecane and BENTONE Gel ISD V this mixture should then be milled in either a colloid or roller mill. | |
| | Suppliers and Trademark Owners | |
| | 1. Dow Corning Corporation   5. Presperse LLC | |
| | 2. Frank B. Ross Company, Inc.   6. Elementis Specialties | |
| | 3. Jeen International Corporation   7. Brenntag Specialties Inc. | |
| | 4. BASF | |

Nail Enamel

| Phase | Ingredients | % w/w |
|---|---|---|
| A | Nail Enamel Base (Butyl Acetate (and) Toluene (and) Nitrocellulose (and) Tosylamide/Formaldehyde Resin (and) Isopropyl Alcohol (and) Dibutyl Phthalate (and) Ethyl Acetate (and) Camphor (and) n-Butyl Alcohol (and) Silica (and) Quaterinum-18 Hectorite) | 97.90 |
| B | Red 6 (10.50-15.50% Toluene Free/Formaldehyde Free Color Solution) | 1.10 |
| | Pearlescent and iridescent pigments | |
| | Inventive Black from examples 1, 3, 4 and/or 6 (Mica/SnO2/Fe3O4, (Mica/SnO$_2$/Fe$_3$O$_4$/SiO$_2$, Mica/SnO$_2$/Fe$_3$O$_4$/TiO$_2$, perlite/SnO$_2$/Fe$_3$O$_4$/SiO$_2$) | 0.20 |
| | Gemtone ® Tan Opal G005 (Mica (and) Titanium Dioxide (and) Iron Oxides) [1] | 0.80 |
| | Procedure | |
| | I. Add Phase A in an appropriate size vessel fitted with a propeller mixer. | |
| | II. Add Phase B to Phase A mixing until batch is uniform. | |
| | III. Fill into containers. | |
| | Suppliers and Trademark Owners | |
| | 1. BASF | |

Pressed Powder Eye Shadow

| Phase | Ingredients | % w/w |
|---|---|---|
| A | Bi-Lite ® 20 (Mica (and) Bismuth Oxychloride) [1] (q.s to 100%) | 21.50 |
| | Kaolin (HUBER 90) [2] | 15.00 |
| | Microcrystalline Cellulose (AVICEL PC 105) [3] | 12.50 |
| | Pearlescent and iridescent pigments | |
| | Inventive Black from examples 1, 3, 4 and/or 6 (Mica/SnO2/Fe3O4, (Mica/SnO$_2$/Fe$_3$O$_4$/SiO$_2$, Mica/SnO$_2$/Fe$_3$O$_4$/TiO$_2$, perlite/SnO$_2$/Fe$_3$O$_4$/SiO$_2$) | 9.50 |
| | Gemtone ® Tan Opal G005 (Mica (and) Titanium Dioxide (and) Iron Oxides) [1] | 28.50 |
| B | *Crambe Abyssinica* Seed Oil (and) *Butyrospermum Parkii* (Shea Butter) Extract (FANCOL ABYSHEA) [4] | 7.50 |
| | *Simmondsia Chinensis* (Jojoba) Seed Oil | 1.50 |
| | *Cocos Nucifera* (Coconut) Oil | 1.00 |
| | Antioxidant | q.s. |
| | Preservatives | q.s. |
| C | Reflecks ™ Dimensions Sparkling Blue G630D (Calcium Sodium Borosilicate (and) Titanium Dioxide) [1] | 3.00 |
| | Procedure | |
| | I. Thoroughly blend Phase A in appropriate dry blending/dispersing equipment. | |
| | II. Pre-disperse Phase B until uniform. | |
| | III. Spray Phase B into Phase A. Pulverize and return to blender. | |
| | IV. Add Phase C to Phase AB. Tumble until uniform. | |
| | V. Press. | |
| | Suppliers and Trademark Owners | |
| | 1. BASF   3. FMC Corporation | |
| | 2. J.M. Huber Corporation   4. Fancor Ltd. | |

-continued

| Shampoo | | |
|---|---|---|
| Phase | Ingredients | % w/w |
| A | DI Water (q.s. to 100%) | 15.40 |
|   | Acrylates/Aminoacrylates/C10-30 Alkyl PEG-20 Itaconate Copolymer (STRUCTURE PLUS) [1] | 7.00 |
| B | DI Water | 15.00 |
|   | Comperlan ®100 (Cocamide MEA) [2] | 0.50 |
| C | Texapon ® NSO (Sodium Laureth Sulfate) [2] | 35.70 |
|   | Cocamidopropyl Betaine (TEGO BETAIN L 7) [3] | 13.50 |
|   | Disodium Laureth Sulfosuccinate (REWOPOL SBFA 30B) [3] | 7.80 |
|   | Luviquat ® Sensation (Polyquaternium-87) [4] | 1.84 |
|   | Preservatives | q.s. |
|   | Fragrance (Spring Flower # 0794029) [4] | 0.500 |
|   | Pearlescent and iridescent pigments | |
|   | Inventive Black from examples 1, 3, 4 and/or 6 (Mica/SnO2/Fe3O4, (Mica/SnO$_2$/Fe$_3$O$_4$/SiO$_2$, Mica/SnO$_2$/Fe$_3$O$_4$/TiO$_2$, perlite/SnO$_2$/Fe$_3$O$_4$/SiO$_2$) | 0.16 |
|   | Blue 1 (1% Aqueous Solution) | 0.25 |
| D | Citric Acid (10% Aqueous Solution) | 2.35 |
|   | Procedure | |
|   | I. Weight out components of Phase A and Phase B separately and stir until the solution is homogeneous. | |
|   | II. Add Phase B to Phase A and stir until uniform. | |
|   | III. Add Phase C to Phase AB and stir until uniform. | |
|   | IV. Adjust pH to 5.6 with citric acid with constant stirring. | |
|   | Suppliers and Trademark Owners | |
|   | 1. National Starch & Chemical Company 3. Evonik Industries | |
|   | 2. BASF 4. Bell Flavors & Fragrances, Inc. | |

| Spray Highlighter | | |
|---|---|---|
| Phase | Ingredients | % w/w |
| A | SD Alcohol 40 B (Alcohol Denatured) [2] | 55.00 |
|   | Aminomethyl Propanol (AMP-95) [3] | 0.88 |
|   | MEA Borate (and) MIPA Borate (MONACOR BE) [4] | 0.05 |
|   | Uvinul ® MC 80 (Ethyhexyl Methoxycinnamate) [1] | 0.05 |
|   | Cyclopentasiloxane (DOW CORNING 245 Fluid) [5] | 0.10 |
|   | D-Panthenol 75W (Panthenol) [1] | 0.10 |
|   | Cucumber TEA 862157 (Fragrance) [6] | 0.10 |
|   | Luvimer ® 100P (Acrylates Copolymer) [1] | 2.00 |
|   | Ultrahold ® Strong (Acrylates Copolymer) [1] | 3.00 |
| B | Chione ™ Snowfall White S130D (Synthetic Fluorphlogopite (and) Titanium Dioxide) [7] | 0.10 |
|   | Pearlescent and iridescent pigments | |
|   | Inventive Black from examples 1, 3, 4 and/or 6 (Mica/SnO2/Fe3O4, (Mica/SnO$_2$/Fe$_3$O$_4$/SiO$_2$, Mica/SnO$_2$/Fe$_3$O$_4$/TiO$_2$, perlite/SnO$_2$/Fe$_3$O$_4$/SiO$_2$) | 0.90 |
| C | Hydroflourocarbon 152A [7] | 37.72 |
|   | Procedure | |
|   | I. Mix all ingredients in order shown with adequate agitation. | |
|   | II. Fill into appropriate containers and charge with propellant. | |
|   | Aerosol Density: 0.85 g/mL | |
|   | Vapor Pressure @ ambient: 55 psig | |
|   | Packaging | |
|   | Can: Exal Aluminum Epoxy Lined | |
|   | Valve: Seaquist Perfect Valve XT-96 | |
|   | Body: XT ES BRB 013 ORIF N | |
|   | Stem: 0.013 Virgin Nylon | |
|   | Actuator: XT-150 ES 0.013 Misty | |
|   | Diptube: 0.165 ID" | |
|   | Suppliers and Trademark Owners | |
|   | 1. BASF 5. Dow Corning Corporation | |
|   | 2. AAPER Alcohol and Chemical Co. 6. Drom Fragrances, Inc. | |
|   | 3. Dow Chemical Company 7. DuPont Company | |

| Elegant Sun Protection | | |
|---|---|---|
| Phase | Ingredients | % w/w |
| A | DI Water | 38.10 |
|   | D-Panthenol 75W (Panthenol) [1] | 1.00 |
|   | Pluracare ® E 400 NF (PEG-8) [1] | 2.50 |
|   | Edeta ® BD (Disodium EDTA) [1] | 0.10 |
|   | Luvigel ® STAR (Polyurethane-39) [1] | 2.50 |
| B. | Uvinul ® T 150* (Octyltriazone) [1] | 2.00 |
|   | Tinosorb ® S* (Bemotrizinol) [1] | 3.00 |
|   | Cetiol ® Sensoft (Propylheptyl Caprylate) [2] | 5.00 |
|   | Cetiol ® CC (Dicaprylyl Carbonate) | 5.00 |
| C | Cremophor ® A 25 (Ceteareth-25) [1] | 2.50 |
|   | Cremophor ® GS 32 (Polyglyceryl-3 Distearate) [1] | 2.50 |
|   | Cremophor ® WO-7(PEG-7 Hydrogenated Castor Oil) [1] | 0.50 |
|   | Stearyl Alcohol (LANETTE 18) [2] | 2.50 |

-continued

|   | | % w/w |
|---|---|---|
| | Dimethicone (DOW CORNING 200 FLUID 50 CST) [3] | 1.50 |
| | Luvitol ® Lite (Hydrogenated Polyisobutene) [1] | 1.50 |
| | Vitamin E Acetate Care (Tocopherol Acetate) [1] | 0.50 |
| | Bisabolol Racemic (Bisabolol) [1] | 1.00 |
| D | DI Water | 10.00 |
| | Tinosorb ® M* (Bisoctrizole) | 10.00 |
| E | DI Water (q.s. to 100%) | 5.50 |
| | Cloisonné ® Satin Gold 262MC (Mica (and) Titanium Dioxide (and) Iron Oxides) | 1.60 |
| | Pearlescent and iridescent pigments | |
| | Inventive Black from examples 1, 3, 4 and/or 6 (Mica/$SnO_2$/$Fe_3O_4$, Mica/$SnO_2$/$Fe_3O_4$/$SiO_2$, Mica/$SnO_2$/$Fe_3O_4$/$TiO_2$, perlite/$SnO_2$/$Fe_3O_4$/$SiO_2$) | 0.20 |
| | Cloisonné ® Satin Bronze 250M (Mica (and) Iron Oxides) [1] | 0.60 |
| | Cloisonné ® Satin Copper 350M (Mica (and) Iron Oxides) [1] | 0.20 |
| F | Fragrance (ORANGE NECTAR FRAG. AD78-00997) [4] | 0.20 |
| | Preservatives | q.s. |

* Note: Tinosorb S, Tinosorb M and Uvinul T 150 are not an approved Sunscreen active in the USA and Canada.

Procedure
- I. Combine Phase A and heat to 75-80° C.
- II. Pre-mix Phase B and heat to 75-80° C.
- III. Combine Phase C and heat to 75-80° C.
- IV. Add Phase B to Phase C while at 75-80° C. and mix well.
- V. Add Phase BC to Phase A and homogenize for 2-3 minutes while at 75-80° C. at low speed.
- VI. Transfer to sweep mixing and start cooling.
- VII. Pre-mix Phase D and add to the batch at 50° C. or below.
- VIII. Pre-mix Phase E and add to the batch, then mix well.
- IX. Add Phase F one by one and mix well, then stop.

Suppliers and Trademark Owners
1. BASF
2. COGNIS
3. Dow Corning Corporation
4. Ungerer & Company

Talc Free Mineral Bronzer

| Phase | Ingredients | % w/w |
|---|---|---|
| A | Mearlmica ® SVA (Mica (and) Lauroyl Lysine) [1] (q.s. to 100%) | 36.500 |
| | Flamenco ® Sparkle Red 420J (Mica (and) Titanium Dioxide) [1] | 15.000 |
| | Z-Cote ® (Zinc Oxide) [1] | 15.000 |
| | Cloisonné ® Satin Bronze (Mica (and) Iron Oxides) [1] | 20.000 |
| | Pearlescent and iridescent pigments | |
| | Inventive Black from examples 1, 3, 4 and/or 6 (Mica/$SnO_2$/$Fe_3O_4$, Mica/$SnO_2$/$Fe_3O_4$/$SiO_2$, Mica/$SnO_2$/$Fe_3O_4$/$TiO_2$, perlite/$SnO_2$/$Fe_3O_4$/$SiO_2$) | 3.500 |
| | Boron Nitride Powder (Boron Nitride) [2] | 5.000 |
| B | Luvitol ® Lite (Hydrogenated Polyisobutene) [1] | 2.500 |
| | Octyldodecyl Neopentanoate (Elefac I-205) [3] | 2.500 |
| | Antioxidants | q.s. |
| | Preservatives | q.s. |

Procedure
- I. Thoroughly blend Phase A in appropriate dry blending/dispersing equipment.
- II. Pre-disperse Phase B and spray into Phase A.
- III. Pulverize and package into appropriate containers.

Suppliers and Trademark Owners
1. BASF
2. ESK Ceramics
3. Alzo International, Inc.

While the compositions and their methods of use have been disclosed with reference to specific embodiments, it is apparent that other embodiments and variations may be devised by others skilled in the art without departing from the true spirit and scope of the described compositions, kits and methods of use. The appended claims are intended to be construed to include all such embodiments and equivalent variations.

What is claimed is:

1. A black effect pigment comprising
   a) at least a partial layer of $SnO_2$ and/or hydrated $SnO_2$ on a substrate,
   b) at least a partial layer of $Fe_3O_4$, and
   c) optionally, a further layer of metal oxide,
   wherein the at least partial layer of $Fe_3O_4$ may further contain ferric hydroxide and $Fe_2O_3$, and the $SnO_2$ and/or $SnO_2$ hydrate ranges from 0.5 to 4 wt. % and the $Fe_3O_4$ ranges from 18.4 to about 70 wt % and the wt. % is based on the total weight of the black effect pigment.

2. The black effect pigment of claim 1, wherein the $SnO_2$ and/or hydrated $SnO_2$ layer and/or the $Fe_3O_4$ layer encapsulates or forms a continuous coating or layer on the substrate.

3. The pigment of claim 1, which further layer c) is selected from the metal oxide group consisting of $SiO_2$, $TiO_2$, $ZrO_2$, $Al_2O_3$ and ZnO.

4. The pigment of claim 3, wherein the metal oxide is $SiO_2$ or $TiO_2$.

5. The pigment of claim 1, wherein the pigment contains a metal oxide layer c) and the metal oxide layer is transparent.

6. The pigment of claim 1, wherein the substrate is selected from the group consisting of aluminum oxide, platy glass, perlite, aluminum, natural mica, synthetic mica, bismuth oxychloride, platy iron oxide, platy graphite, bronze, stainless steel, natural pearl, boron nitride, silicon dioxide, copper flake, copper alloy flake, zinc flake, zinc alloy flake, zinc oxide, enamel, china clay, porcelain, titanium oxide, titanium dioxide, titanium suboxides, zeolite, kaolin, zeolites and combinations thereof.

7. The pigment of claim 1, wherein the substrate is selected from the group consisting of natural mica, synthetic mica, perlite, platy glass and aluminum.

8. The pigment of claim 1, with the proviso that the $SnO_2$ and/or $SnO_2$ hydrate coating or layer is not incorporated into a $TiO_2$ coating or layer.

9. The pigment of claim 1, wherein the substrate is mica or synthetic mica.

10. The pigment of claim 1, wherein the $SnO_2$ and $Fe_3O_4$ are present in the same layer.

11. The pigment of claim 1, wherein the $SnO_2$ and $Fe_3O_4$ are present in two separate layers.

12. The pigment of claim 1, which has the following layer structure:
   substrate/$SnO_2$ and/or $SnO_2$ hydrate+$Fe_3O_4$ (in same layer)
   substrate/$SnO_2$ and/or $SnO_2$ hydrate+$Fe_3O_4$ (in same layer)/$SiO_2$
   substrate/$SnO_2$ and/or $SnO_2$ hydrate/$Fe_3O_4$
   substrate/$SnO_2$ and/or $SnO_2$ hydrate/$Fe_3O_4$/$SiO_2$
   substrate/$SnO_2$ and/or $SnO_2$ hydrate/$Fe_3O_4$/$TiO_2$
   substrate/$SnO_2$ and/or $SnO_2$ hydrate/$Fe_3O_4$/$ZnO_2$
   substrate/$SnO_2$ and/or $SnO_2$ hydrate/$Fe_3O_4$/$ZrO_2$
   substrate/$TiO_2$+$SnO_2$/$Fe_3O_4$/$SiO_2$
   substrate/$SnO_2$ and/or $SnO_2$ hydrate/$TiO_2$+$SnO_2$/$Fe_3O_4$/$SiO_2$
   substrate/$TiO_2$+$SnO_2$/$SnO_2$ and/or $SnO_2$ hydrate/$Fe_3O_4$/$SiO_2$
   substrate/$SnO_2$ and/or $SnO_2$ hydrate/$Fe_3O_4$/$TiO_2$+$SnO_2$/$Fe_3O_4$/$SiO_2$
   substrate/$SnO_2$ and/or $SnO2$ hydrate/$Fe_3O_4$/$SiO_2$/$SnO_2$/$Fe_3O_4$/$SiO_2$
   substrate/$SiO_2$/$SnO_2$ and/or $SnO_2$ hydrate/$Fe_3O_4$/$TiO_2$, or
   substrate/$SnO_2$/$TiO_2$/$SnO_2$/$Fe_3O_4$/$SiO_2$,
   wherein the substrate is selected from the group consisting of aluminum oxide, platy glass, perlite, aluminum, natural mica, synthetic mica, bismuth oxychloride, platy iron oxide, platy graphite, bronze, stainless steel, natural pearl, boron nitride, silicon dioxide, copper flake, copper alloy flake, zinc flake, zinc alloy flake, zinc oxide, enamel, china clay, porcelain, titanium oxide, titanium dioxide, titanium suboxide, zeolite, kaolin, borosilicate and combinations thereof.

13. A paint, coating, powder coating, printing ink, laser marking pigment, cosmetic formulation, pigment composition or dry preparation comprising the black effect pigment according to claim 1.

14. A cosmetic formulation comprising the black effect pigment according to claim 1.

15. The cosmetic formulation according to claim 14, which further contains from about 10 to about 90 wt. % a cosmetically suitable carrier material.

16. The cosmetic formulation according to claim 14, wherein the formulation is a cosmetic product selected from concealing sticks, foundations, stage make-up, mascaras, cake mascaras, cream mascaras, eye shadows, liquid eye shadows, pomade eye shadows, powder eye shadows, stick eye shadows, pressed eye shadows, cream eye shadows, hair color, lipsticks, lip gloss, kohl pencils, eye liners, blushers, eyebrow pencils, cream powders, nail enamels, skin glosser stick, hair sprays, face powders, leg-makeup, insect repellent lotion, nail enamel remover, perfume lotion, shampoos, gel shampoos, liquid shampoos, shaving creams, aerosol shaving creams, brushless shaving creams, lathering shaving creams, hair grooming products, cologne sticks, colognes, cologne emollients, bubble baths, body lotions, moisturizing body lotions, cleansing body lotions, analgesic body lotions, astringent body lotions, after shave lotions, after bath milks and sunscreen lotions.

17. A method of preparing the black effect pigment according to claim 1, comprising the steps of
   applying a coating or layer of $Fe_3O_4$ which may further include ferric hydroxide or ferric oxide, onto an at least partially coated or layered $SnO_2$ which may further include hydrated $SnO_2$ coated substrate and optionally applying a further metal oxide coating.

18. The method according to claim 17, wherein the substrate is selected from the group consisting of aluminum oxide, platy glass, perlite, aluminum, natural mica, synthetic mica, bismuth oxychloride, platy iron oxide, platy graphite, platy silica, bronze, stainless steel, natural pearl, boron nitride, copper flake, copper alloy flake, zinc flake, zinc alloy flake, zinc oxide, enamel, china clay, porcelain, titanium oxide, titanium dioxide, titanium suboxides, zeolites, kaolin and combinations thereof.

19. A method of increasing the adhesion of $Fe_3O_4$ to a substrate comprising
   the steps of a) at least partially coating the substrate with from 0.5 to 4 wt. %
   $SnO_2$ or hydrated $SnO_2$,
   b) applying from 18.4 to about 70 wt % of
   $Fe_3O_4$ to the at least partially coated substrate of step a) and
   c) optionally, applying a further metal oxide coating
   and the wt. % is based on the total weight of the coated substrate.

20. The pigment of claim 1, wherein the $SnO_2$ and/or $SnO_2$ hydrate partially or completely coats said substrate and is adjacently and directly coated with at least a partial coating or layer of $Fe_3O_4$.

* * * * *